United States Patent
Ziermann et al.

(10) Patent No.: US 6,177,262 B1
(45) Date of Patent: Jan. 23, 2001

(54) RECOMBINANT HOST CELLS FOR THE PRODUCTION OF POLYKETIDES

(75) Inventors: Rainer Ziermann, San Mateo; Mary C. Betlach, San Francisco, both of CA (US)

(73) Assignee: Kosan Biosciences, Inc., Hayward, CA (US)

( * ) Notice: Under 35 U.S.C. 154(b), the term of this patent shall be extended for 0 days.

(21) Appl. No.: 09/181,833

(22) Filed: Oct. 28, 1998

Related U.S. Application Data

(60) Provisional application No. 60/101,557, filed on Sep. 22, 1998.

(51) Int. Cl.$^7$ .................................................. C12P 19/62
(52) U.S. Cl. ........................................ 435/76; 435/252.35
(58) Field of Search ............................ 435/76, 200, 252, 435/35

(56) References Cited

U.S. PATENT DOCUMENTS

| | | | |
|---|---|---|---|
| 4,672,491 | 6/1987 | Koenig et al. | 340/106 |
| 4,744,350 | 5/1988 | Sato | 128/57 |
| 5,098,837 | 3/1992 | Beckmann et al. | 435/76 |
| 5,272,474 | 12/1993 | Hilliard | 340/825.08 |
| 5,364,781 | * 11/1994 | Hutchinson et al. | 435/193 |
| 5,672,491 | * 9/1997 | Khosla et al. | 435/148 |
| 5,672,497 | 9/1997 | Cox et al. | 435/320.1 |
| 5,712,146 | 1/1998 | Khosla et al. | 435/252.35 |

FOREIGN PATENT DOCUMENTS

| | | |
|---|---|---|
| 0 791 656 | 2/1997 | (GB) . |
| WO 93/13663 | 1/1992 | (WO) . |
| WO 97/02358 | 7/1996 | (WO) . |
| WO 98/27203 | 12/1997 | (WO) . |
| WO 99/03986 | 7/1998 | (WO) . |

OTHER PUBLICATIONS

Stuntzman–Engwall et al. Regulation of Secondary Metabolism in Streptomyces spp. and Overproduction of Daunorubicin in Streptomyces peucetius. *J. of Bacteriol.* (1992) 174(1): 144–154.*

Rowe et al. Construction of new vectors for high–level expression in actinomycetes. Gene (1998) 216:215–223, Aug. 1998.*

Kealey et al. "production of a polyketide natural product in nonpolyketide producing prokaryotic and eukaryotic hosts", *Proc. Natl. Acad. Sci., USA*, 95:505–509 (1998).

Kieser et al, A mutation of *Streptomyces lividans* which prevents intraplasmid recombination has no effect on chromosomal recombination, *Mol. Gen.Genet.*, 220(1):60–64 (Dec. 1989).

Li et al., "Cloning, purification, and properties of a phosphotyrosine protein phosphatase from *Streptomyces coelicolor* A3(2)", *J. Bacteriology*, 178(1):136–142 (Jan. 1996).

McDaniel et al., 1993 "Engineered biosynthesis of novel polyketides", *Science* 262:1546–1550 (1993).

Tsai et al, "Isolation and characterization of *Streptomyces lividans* mutants deficient in intraplasmid recombination", *Mol. Gen. Genet.*, 208:211–218 (1987).

Umeyama et al., "Expression of the *Streptomyces coelicolor* A3(2) ptpA gene encoding a phosphotyrosine protein phosphatase leads to overproduction of secondary metabolites in *S. lividans*", *FEMS Microbiology Letters*, 144:177–184 (1996).

* cited by examiner

*Primary Examiner*—Ponnathapu Achutamurthy
*Assistant Examiner*—Kathleen Kerr
(74) *Attorney, Agent, or Firm*—Kevin Kaster; Kate H. Murashige; Carolyn Favorito

(57) ABSTRACT

Yields of polyketides produced in host cells such as Streptomyces can be increased by coexpression of the ptpA gene. The introduction of recombinant vectors encoding ptpA and polyketide synthase genes is more efficient and does not require methyl-free DNA if the host cell is a restriction/methylation deficient strain, such as *Streptomyces lividans* K4-114, K4-155, or K27-39.

13 Claims, No Drawings

RECOMBINANT HOST CELLS FOR THE PRODUCTION OF POLYKETIDES

CROSS-REFERENCE TO RELATED APPLICATIONS

This application claims priority under 35 U.S.C. §119 from provisional application 60/101,557, filed Sep. 22, 1998, inventors Rainer Ziermann and Mary Betlach, which is incorporated herein by reference.

REFERENCE TO GOVERNMENT FUNDING

This work herein described was supported at least in part by the U.S. government under SBIR grant 1R43 CA 75792-01. The U.S. government has certain rights in this invention.

FIELD OF THE INVENTION

The present invention provides recombinant host cells and methods for producing polyketides. Polyketides are a diverse class of compounds with a wide variety of activities, including activities useful for medical, veterinary, and agricultural purposes. The present invention therefore relates to the fields of molecular biology, chemistry, recombinant DNA technology, medicine, animal health, and agriculture.

BACKGROUND OF THE INVENTION

Polyketides have been produced in a variety of host cells, including Streptomyces, Saccharopolyspora, and Aspergillus for commercial purposes for many years. In particular, these compounds are often found in mycelial bacteria, the actinomycetes, in which the compounds are synthesized by enzymes known as polyketide synthases (PKSs) and produced as secondary metabolites. Typically, a polyketide was first identified as an active but uncharacterized ingredient in a soil or other environmental sample. Once an active ingredient was identified, then the organism that produced the ingredient was isolated and characterized. After the organism was characterized, it was often the subject of an intensive effort to increase the yield of the active ingredient. This effort typically involved successive rounds of subjecting the organism to mutagenic conditions, culturing the mutagenized organisms, and selecting those mutant organisms that produced the active ingredient in higher yields.

With the advent of molecular biology, the genes for the enzymes, called polyketide synthases or PKS(s), that perform the synthesis of certain polyketides became known. In some instances, such as, for example, the PKS enzymes that catalyze the synthesis of modular polyketides, the PKS enzymes are very large, multi-subunit proteins encoded by large gene clusters ranging from 10 kilobases (kb) to more than 100 kb in size. See, e.g., PCT patent publication No. 93/13663 (erythromycin); U.S. Pat. No. 5,098,837 (tylosin); U.S. Pat. No. 5,272,474 (avermectin); U.S. Pat. No. 5,744,350 (triol polyketide); and European patent publication No. 791,656 (platenolide), each of which is incorporated herein by reference. The cloning of these and other genes led to speculation that the yields of polyketide produced by these organisms could be increased by molecular biology techniques. See, e.g., U.S. Pat. No. 5,672,497. Despite these advances, however, there have been few, if any, reports of polyketide-producing strains that have been improved using such techniques.

Others working in the field developed novel methods and host cells not only for producing polyketides in host cells in which naturally occurring polyketide synthase genes had been eliminated or which otherwise did not produce polyketides but also for producing polyketides not otherwise found in nature in recombinant host cells. Thus, 6-deoxyerythronolide B has been produced in a *Streptomyces coelicolor* strain from which the endogenous actinorhodin gene cluster has been eliminated. See U.S. Pat. Nos. 5,672,491 and 5,712,146 and McDaniel et al., 1993, Engineered biosynthesis of novel polyketides, *Science* 262:1546–1550, each of which is incorporated herein by reference. In addition, the successful synthesis of a fungal polyketide, 6-methylsalicylic acid (6-MSA), has been reported in *E. coli* and in yeast. See Kealey et al., 1998, Production of a polyketide natural product in nonpolyketide producing prokaryotic and eukaryotic hosts, *Proc. Natl. Acad. Sci. USA* 95:505–509, and PCT patent publication No. 98/27203, incorporated herein by reference. Also, methods, reagents, and host cells were developed for producing novel polyketides from starting units not used by polyketide producing organisms in nature. See PCT patent publication No. 97/02358 and PCT patent application No. US98/14911. While the novel polyketides produced by such methods and cells were useful, yields were sometimes low, and rapid application of the technology in new host cells was sometimes hindered by endogenous recombination pathways and restriction—modification systems.

As one example, Kieser et al., December 1989, A mutation of *Streptomyces lividans* which prevents intraplasmid recombination has no effect on chromosomal recombination, *Mol. Gen. Genet.* 220(1): 60–64, reported on a recombination-deficient strain of *S. lividans*, JT46, originally characterized by Tsai and Chen, 1987, Isolation and characterization of *Streptomyces lividans* mutants deficient in intraplasmid recombination, *Mol. Gen. Genet.* 208: 211–218. This strain, however, produced the pigmented antibiotic actinorhodin produced by the unmodified parent strain *S. lividans* and so is not especially preferred for the production of other polyketides.

Other researchers have noted that actinorhodin as well as undecylprodigiosin and A-factor levels can be increased in *Streptomyces lividans* by transforming the strain with a vector having a copy number of 3–4 (but not 1–2) and encoding a phosphotyrosine protein phosphatase gene (ptpA) with its endogenous promoter isolated from *S. coelicolor*. See Umeyama et al., 1996, Expression of the *Streptomyces coelicolor* A3(2) ptpA gene encoding a phosphotyrosine protein phosphatase leads to overproduction of secondary metabolites in *S. lividans*, *FEMS Microbiology Letters* 144: 177–184; and Li and Strohl, January 1996, Cloning, purification, and properties of a phosphotyrosine protein phosphatase from *Streptomyces coelicolor* A3(2), *J. Bacteriology* 178(1): 136–142. Unfortunately, actinorhodin has little if any therapeutic value.

There remains a need for host cells that can produce useful polyketides at higher levels than can be achieved with currently available cells, as well as a need for cells that can be transformed at high efficiency and can stably maintain extrachromosomal plasmids containing polyketide synthase genes over many generations. The present invention meets these and other needs.

SUMMARY OF THE INVENTION

In one embodiment, the present invention provides a *Streptomyces lividans* host cell that can be transformed at high efficiency with methylated DNA and that does not produce actinorhodin. In a preferred mode, this host cell is *S. lividans* K4-114 or K4-155.

In another embodiment, the present invention provides a *Streptomyces lividans* host cell that lacks an ability to recombine plasmid DNA with other plasmid DNA. In a preferred mode, this host cell is S. lividans K27-39.

In another embodiment, the invention provides a method for increasing production of a polyketide other than actinorhodin or undecylprodigiosin in a host cell that produces said polyketide, said method comprising steps of: (a) transforming said host cell with a recombinant vector that comprises a ptpA gene capable of expression in said host cell; and (b) culturing said host cell transformed in step (a) under conditions such that said ptpA gene is expressed and said polyketide is produced. The ptpA gene may be under the control of its endogenous promotor or may be controlled by a heterologous promoter. In a preferred mode, the ptpA gene is under the control of a heterologous promoter from a polyketide biosynthetic gene. In an especially preferred mode the promoter is the actI promoter. The recombinant vector can be an integrating or extrachromosomally maintained vector.

In a preferred mode, the method is practiced with a Streptomyces host cell, such as S. coelicolor or S. lividans, including, but not limited to S. coelicolor CH999, S. lividans K4-114, S. lividans K4-155, and S. lividans K27-39. In another preferred mode, the polyketide is produced by a recombinant polyketide synthase. In another preferred mode, the recombinant polyketide synthase is encoded on a plasmid in said host cell. In a very preferred mode, the polyketide is erythromycin or an erythromycin precursor (i.e., 6-deoxyerythronolide B) that is produced from a recombinant polyketide synthase that differs from an erythromycin PKS by substitution, insertion, or deletion of one or more amino acid residues. As one example, the erythromycin precursor can be 10,11-anhydro, 6-deoxyerythronolide B.

These and other embodiments, modes, and aspects of the invention are described in more detail in the following description, the examples, and claims set forth below.

DETAILED DESCRIPTION OF THE INVENTION

Efficient polyketide synthesis derived from plasmid-borne heterologous polyketide synthase gene clusters necessitates a suitable host strain. Well characterized laboratory strains such as *Streptomyces coelicolor* or *S. lividans* and their frequently used derivatives carry endogenous genes for the synthesis of actinorhodin, which can interfere with the efficient production of extrachromosomally encoded PKS proteins and the quantitative analysis of their secreted polyketide products. To circumvent this problem, McDaniel et al., supra, engineered a *S. coelicolor* derivative, CH999, in which the actinorhodin gene cluster has been substantially deleted. However, this strain can be transformed only with methyl-free DNA, and, unlike its otherwise isogenic parent CH1, exhibits low transformability.

*E. coli*/Streptomyces shuttle vectors harboring PKS gene clusters frequently are larger than 20 kb in size. Large plasmid size results in decreased transformation frequencies, relative to smaller plasmids. Thus, host strains that can be efficiently transformed, preferably with methylated DNA, are preferred for the production of polyketides from plasmid-borne recombinant PKSs.

The present invention provides *Streptomyces lividans* host cells that substantially lack the actinorhodin gene cluster and so do not produce actinorhodin. These host cells can be transformed with methylated DNA at high efficiency. In particular, the invention provides two preferred *S. lividans* host strains, K4-114 and K4-155.

*Streptomyces coelicolor* CH999 was constructed by a recombination procedure using a shuttle vector that carries a temperature sensitive Streptomyces origin of replication that resulted in the deletion of the actinorhodin gene cluster through double crossover recombination.

Two similar approaches were used to construct analogous *Streptomyces lividans* strains, as described below and in more detail in Example 1. In the first approach, the procedure of McDaniel et al., supra, was followed in that TK24 protoplasts were transformed with *E. coli*/Streptomyces shuttle vector, pLRermEts, and transformants were selected at 30° C. for resistance to thiostrepton. This selection permits independent replication of this plasmid that carries a temperature sensitive Streptomyces replicon derived from pSG5. See Muth et al., 1989, A vector system with temperature-sensitive replication for gene disruption and mutational cloning in streptomycetes, *Mol. Gen. Genet.* 219:341–348. The ermE gene product causes resistance to lincomycin.

Individually picked colonies were subsequently restreaked on plates containing lincomycin and lacking thiostrepton and incubated at 39° C. Because the autonomous plasmid cannot efficiently replicate at the elevated temperature, this temperature shift selects for clones that harbor a chromosomally integrated copy of the plasmid. Homologous recombination between one (or both) of the two plasmid borne actinorhodin gene fragments flanking ermE with its homologous counterpart in the host chromosome leads to integration in the actinorhodin gene cluster.

Several clones were obtained that failed to exhibit the characteristic blue phenotype of actinorhodin production: these clones were presumed to lack actinorhodin production. These clones were pink in color due to the synthesis of undecylprodigiosin, another pigmented antibiotic known to be produced by *S. lividans*. These clones were tested for their antibiotic resistance phenotypes, and three clones were identified that were resistant to lincomycin but sensitive to thiostrepton, consistent with a deletion of the actinorhodin gene cluster due to two recombination events between the homologous actinorhodin gene fragments.

In the second approach, TK24 was transformed with pKOS4-149, and the transformants were directly selected for lincomycin resistance. Plasmid pKOS4-149 is a pBluescriptSK$^-$ (Stratagene, San Diego) derivative that carries the same DNA fragment of ermE flanked by actinorhodin gene sequences as used in the first approach, as well as the tsr gene, but the plasmid cannot replicate in the Streptomyces host, i.e. the plasmid constitutes a suicide plasmid. Thus, any transformants should carry an integrated copy of either the entire plasmid or at least the fragment carrying ermE. Several clones were obtained that were resistant to lincomycin yet sensitive to thiostrepton and did not produce actinorhodin. This phenotype is consistent with a successful replacement of the actinorhodin gene cluster by ermE due to a double crossover event.

The *S. coelicolor* actinorhodin deficient strain CH999 can be transformed with an efficiency of up to $10^3$ transformants/μg DNA, dependent on plasmid size, well below the reported transformation efficiencies of $10^6$–$10^7$ transformants/μg DNA for wild-type *S. coelicolor* and *S. lividans* (see Hopwood et al., supra). Thus, *S. lividans* TK24 (see Hopwood et al., supra), a streptomycin resistant, plasmid-free derivative of *S. lividans* 66, can be transformed more than 100-fold better than *S. coelicolor* CH999. The present invention provides act$^-$ mutants of *S. lividans* TK24 that exhibit high transformability, as described in Example 2.

As described in Example 3, the *S. lividans* strains of the invention can be used to produce polyketides from recombinant PKS genes at levels equating those produced in CH999. Upon transformation with an appropriate expression vector, CH999, K4-114, and K4-155 each equally well produce the erythromycin precursor 6-deoxyerythronolide B (6-dEB). In summary, the *S. lividans* actinorhodin minus strains of the invention can be transformed at high efficiency by both methylated and unmethylated DNA and yield significant quantities of macrolides produced by plasmid borne recombinant polyketide synthases. These strains are thus preferred host strains for the production of bioengineered polyketides.

Another *Streptomyces lividans* host strain of the invention especially preferred for the production of bioengineered polyketides produced by recombinant polyketide synthase enzymes is deficient in its ability to perform inter- and intraplasmid recombination as well as its ability to produce actinorhodin. Thus, this strain is ideally suited for the production of polyketides from recombinant polyketide synthases that are encoded by two or more autonomously replicating vectors in a recombinant host cell or involve the use of an otherwise unstable plasmid. Such multi-vector production is especially preferred for the production of novel polyketides by recombinant polyketide synthases produced in libraries. See PCT patent publication No. 98/27203, incorporated herein by reference.

This strain, designated *Streptomyces lividans* K27-39, was derived from an *S. lividans* strain deficient in intraplasmid recombination and designated JT46. See Tsai and Chen, 1987, *Mol. Gen. Genet*. 208: 211–218, incorporated herein by reference. The strain allows maintainance of unstably replicating vectors. The JT46 strain has been shown not to prevent homologous recombination between a recombinant plasmid and the host chromosome; the mutation, perhaps in a topoisomerase type I gene, causes a defect that is limited to the prevention of homologous and illegitimate intraplasmid recombination. See Kieser et al., December 1989, A mutation of *Streptomyces lividans* which prevents intraplasmid recombination has no effect on chromosomal recombination, *Mol. Gen. Genet*. 220(1): 60–64, incorporated herein by reference.

Strain JT46 was obtained from Dr. Luis Servin-Gonzalez of University of Mexico City. The K27-39 strain was constructed in a manner analogous to the construction of *Streptomyces coelicolor* CH999 and *S. lividans* K4-114 (see Example 1, below), i.e., the actinorhodin gene cluster in JT46 was deleted using pLRermEts. Strain K27-39 does not produce actinorhodin and carries integrated in the chromosome the ermE gene encoding resistance to lincomycin. See Example 4.

These strains of the invention can be employed in the method provided by the present invention for increasing the yield of polyketide from a polyketide producing host cell. The strains are especially preferred for application in this method if the polyketide to be produced is synthesized with a recombinant PKS encoded on an autonomously replicating vector.

The method for increasing polyketide production provided by the invention relates to the coexpression of an enzyme, phosphotyrosine protein phosphatase A (ptpA), with the polyketide synthase that produces the desired polyketide. The method comprises the steps of: (a) transforming a host cell with a recombinant vector that comprises a ptpA gene capable of expression in said host cell; and (b) culturing said host cell transformed in step (a) under conditions such that said ptpA gene is expressed and said polyketide is produced. This method of the invention is illustrated in Example 5.

While any ptpA gene product may be used, it is especially preferred to use a ptpA gene product endogenous to the host cell in which the polyketide is to be produced. In a preferred embodiment, the ptpA gene product is derived from the open reading frame of the ptpA gene from *Streptomyces lividans* or *S. coelicolor* ptpA gene. See Umeyama et al., supra, and Li and Strohl, slupra. In an especially preferred embodiment, the ptpA gene is located in the polyketide producing host cell either integrated into the chromosome or on a vector with a copy number of 1–2, such as SCP2*.

The ptpA gene may be used with its naturally occurring promoter; however, in a preferred embodiment, the promoter is a heterologous promoter and is derived from a gene that is activated at the same time polyketide production in the cell is induced. In an especially preferred embodiment, the promoter is a heterologous promoter and is itself derived from a PKS gene or gene cluster. Thus, in one highly preferred embodiment, the promoter for the ptpA gene is derived from the actinorhodin gene cluster, i.e., the actI gene promoter, and the actII-ORF4 activator gene is expressed in the host cell.

While any host cell that produces a PKS, whether naturally or by application of recombinant DNA technology, can be employed in the method, in an especially preferred embodiment, the host cell is a Streptomyces host cell. Such host cells are preferred due to the wide variety of polyketides produced by cells of that genus. If the host cell is *S. lividans* or *S. coelicolor*, however, the polyketide is typically a polyketide other than a pigmented antibiotic such as prodigiosin or actinorhodin.

While the method is applicable to the production of any polyketide, in a preferred embodiment, the polyketide is a polyketide produced by a recombinant PKS. Suitable polyketides for production by the method include erythromycin, FK-506, FK-520, oleandomycin, rapamycin, and tylosin. Polyketides suitable for production by the method of the invention that are produced by recombinant PKSs are disclosed, e.g., in U.S. Pat. Nos. 5,672,491 and 5,712,496, and in PCT patent application No. US98/08792 and PCT publication No. 97/02358, each of which is incorporated herein by reference. In an especially preferred embodiment, the recombinant PKS is encoded on an expression vector (either extrachromosomally replicating or integrated into the chromosome of the host cell).

Thus, the present invention provides host cells useful for making polyketides and a method by which the production of polyketides in a host cell can be increased. The following examples are given for the purpose of illustrating the present invention and shall not be construed as being a limitation on the scope of the invention or claims.

EXAMPLE 1

Construction of *Streptomyces lividans* K4-114 and K4-155

A. Materials and Methods

1) Bacterial Strains and Plasmids

*E. coli* XL1-Blue (recA1 endA1 gyrA96 thi-1 hsdR17 supE44 relA1 lac [F' proAB lacI$^q$ZΔM15 Tn10 (Tet$^r$)]) was the preferred plasmid host. *E. coli* SCS110 (rpsL (Str$^r$) thr leu endA thi-1 lacy galK galT ara tonA tsx dam dcm supE44Δ(lac-proAB) [F' traD36 proAB lacI$^q$ZΔM15]) was used for generating methyl-free plasmid DNA. *S. coelicolor* CH1, CH999 and plasmid pLRermEts are described in detail in U.S. Pat. Nos. 5,672,491 and 5,712,146 and McDaniel et al., 1993, Engineered biosynthesis of novel polyketides, Science 262:1546–1550, each of which is incorporated herein by reference. S. lividans TK24 (str-6) is described by Hopwood et al., 1985, Genetic Manipulation of Streptomyces: A Laboratory Manual, The John Innes Foundation, Norwich, U.K., incorporated herein by reference. Plasmid pKAO127'Kan' is an E. coli/Streptomyces shuttle plasmid that expresses the three 6-deoxyerythronolide B synthase (DEBS) genes required for the synthesis of the macrolide 6-dEB. It is derived from pCK7 (See U.S. Pat. Nos. 5,672, 491 and 5,712,146 and Kao et al., 1994, Engineered biosynthesis of a complete macrolactone in a heterologous host, Science 265: 509–5125, each of which is incorporated herein by reference) by insertion of an ~1.3 kb kanamycin resistance-conferring gene cassette into plasmid pCK7's unique HindIII site. Plasmid pBluescriptSK$^-$ is a commercially available, standard cloning vector (Stratagene, USA).

2) Growth Conditions and Genetic Methods

Cloning, E. coli transformation, plasmid isolation, and DNA manipulations were carried out using standard methods (Sambrook et al., 1989, Molecular Cloning: A Laboratory Manual, II ed. Cold Spring Harbor Laboratory Press, incorporated herein by reference). All Streptomyces techniques and media used are as described by Hopwood et al., supra. Chromosomal Streptomyces DNA was prepared from three mL of a liquid culture of the respective strains. PCR conditions were optimized for amplification of GC-rich Streptomyces DNA; in brief, 10% DMSO was added to each sample and the annealing temperature was raised to 65° C.

3) Polyketide Purification

The compound 6-deoxy erythronolide B (6-dEB) was purified from large R5 agar plates (~34 mL agar) essentially as described in Kao et al., supra. Production levels were calculated from total 6-dEB produced from one plate each.

B. Strain Construction

1) Construction of K4-114

Following the procedure of McDaniel et al., TK24 protoplasts were transformed with E. coli/Streptomyces shuttle vector, pLRermEts, and transformants were selected at 30° C. for resistance to thiostrepton. This selection permits independent replication of this plasmid that carries a temperature sensitive Streptomyces replicon derived from pSG5. See Muth et al., 1989, A vector system with temperature-sensitive replication for gene disruption and mutational cloning in streptomycetes, Mol. Gen. Genet. 219: 341–348. The ermE gene product confers resistance to lincomycin. Individually picked colonies were subsequently restreaked on R5 plates with lincomycin (200 µg/mL) and without thiostrepton and incubated at 39° C.

Because the autonomous plasmid cannot efficiently replicate at the elevated temperature, this temperature shift selects for clones that harbor a chromosomally integrated copy of the plasmid. Homologous recombination between one (or both) of the two plasmid borne actinorhodin gene fragments flanking ermE with its homologous counterpart in the host chromosome leads to integration in the actinorhodin gene cluster. Resulting colonies were restreaked approximately every three days for a period of three weeks at the elevated temperature. Several clones were obtained that failed to exhibit the characteristic blue phenotype, indicative of a lack of actinorhodin production. These colonies were pink, due to the synthesis of undecylprodigiosin, another antibiotic known to be produced by S. lividans.

These candidate clones were assayed for their antibiotic resistance phenotypes, and three were identified that were resistant to lincomycin and sensitive to thiostrepton. This phenotype is consistent with a deletion of the actinorhodin gene cluster due to two recombination events between the homologous actinorhodin gene fragments. After verification, verified clones were identified as independent isolates of strain K4-114.

2) Construction of Strain K4-155

In an alternative approach, TK24 was transformed with pKOS4-149, and transformants were directly selected for lincomycin resistance. This pBluescriptSK$^-$-derivative carries the same DNA fragment of ermE flanked by actinorhodin gene sequences, as well as the tsr gene but cannot replicate in the Streptomyces host, i.e., it constitutes a suicide plasmid. Thus, any transformants supposedly carry an integrated copy of either the entire plasmid or at least the fragment carrying ermE. Several clones were obtained that were resistant to lincomycin and sensitive to thiostrepton and did not produce actinorhodin. This phenotype indicates a successful replacement of the actinorhodin gene cluster by ermE due to a double crossover event. After verification, verified clones were identified as independent isolates of strain K4-155.

3) Verification of Constructs

To demonstrate that candidate clones obtained by either procedure indeed carried a deletion (rather than, e.g., a point mutation) PCR analysis was performed with a total of six clones (three each obtained by either procedure). PCR using primers 1 and 2 (Table 1) leads to the synthesis of a 700 bp ermE gene fragment, while PCR using primers 3 and 4 (Table 1) generates a 900 bp fragment that extends from the 3' region of the actinorhodin ketosynthase/acyltransferase gene (actI-ORF1; see Fernandez-Moreno et al., infra) to the 5' region of the actinorhodin chain length factor gene (actI-ORF2; see Fernandez-Moreno et al., infra).

TABLE 1

Oligonucleotides used for PCR

| Oligonucleotide | Sequence (5' to 3') | Location | SEQ ID NO.: |
| --- | --- | --- | --- |
| 5' ermE | tcggcgatcgtggactggtgcctgg | nt. 601–625* | 1 |
| 3' ermE | gtccgccggtccgtccacccccgga | nt. 1300–1276* | 2 |
| 5' act KS/AT | cgcactccggtcagctcgatcaagt | nt. 1106–1130 | 3 |
| 3' act CLF | tcggtggccgtgctgatccggccac | nt. 2006–1982 | 4 |

*according to Dhillon and Leadley, 1990, A repeated decapeptide motif in the c-terminal domain of the ribosomal RNA methyltransferase from the erythromycin producer Saccharopolyspora erythraea, FEBS Lett. 262: 189–193 (accession number: X51891).
according to Fernandez-Moreno et al., 1992, Nucleotide sequence and deduced functions of a set of cotranscribed genes of Streptomyces coelicolor A3(2) including the polyketide synthase for the antibiotic actinorhodin, J. Biol. Chem. 267: 19278–19290 (accession number: X63449).

Five of these six candidate clones analyzed carry ermE and lack the actinorhodin fragment, while the sixth clone contained ermE as well as the actinorhodin fragment. This verified that five of the six clones resulted from a successful gene replacement of the actinorhodin gene cluster with ermE and thus should be identical.

EXAMPLE 2

Transformation Efficiencies of K4-114

Transformation efficiencies of K4-114 were analyzed. Table 2 shows the results of one such experiment, which are typical for the strain. With methyl-free DNA, efficiencies in the range of $10^5$ transformants/µg DNA were obtained, which is at least 100-fold better than the corresponding efficiencies for CH999. In addition, while it is impractical to obtain CH999 transformants using methylated DNA, a slight decrease in transformation efficiencies was observed with methylated as compared to unmethylated DNA, as shown in Table 2. The differing efficiencies reflect different restriction/methylation systems in the coelicolor as compared to lividans strains, as has been reported by Kieser and Hopwood, 1991, Genetic manipulation of Streptomyces: Integrating vectors and gene replacement, Miller (Ed.), Methods in Enzymology, Academic Press, Inc., San Diego, Calif.

TABLE 2

*Streptomyces lividans* K4–114 Transformation Efficiencies

| DNA source | methylated (+)/ methyl-free (−) | Plasmid size in kb | transformants/ μg DNA* |
|---|---|---|---|
| pKAO127'Kan' | + | 48 | $3.5 \times 10^4$ |
| pKAO127'Kan' | − | 48 | $1.3 \times 10^5$ |

EXAMPLE 3

Polyketide Production

To demonstrate that polyketide production levels in strains K4-114 and K4-155 is equivalent to that observed with CH999, these three strains were transformed with pKAO127'Kan', using selection for thiostrepton resistance, which leads to the synthesis of the erythromycin precursor 6-dEB, a well-studied macrolide (see Cortes et al., 1990, An unusually large multifunctional polypeptide in the erythromycin-producing polyketide synthase of *Saccharopolyspora erythraea*. Nature 348:176–178). Production levels of this compound, as detected and quantitated by liquid chromatography mass spectroscopy (LCMS), reproducibly ranged from 10–20 mg/L in K4-114, K4-155 and CH999, respectively. No strain-specific difference in polyketide production was apparent.

EXAMPLE 4

Construction of Strain K27-39

Strain *Streptomyces lividans* JT 46 (Tsai and Chen, supra) was obtained from Dr. Luis Servin-Gonzalez of the University of Mexico City. Following the procedure of McDaniel et al., supra, JT46 protoplasts were transformed with *E. coli*/Streptomyces shuttle vector, pLRermEts, and transformants were selected at 30° C. for resistance to thiostrepton. This selection permits independent replication of this plasmid that carries a temperature sensitive Streptomyces replicon derived from pSG5. See Muth et al., supra. The ermE gene product confers resistance to lincomycin. Individually picked colonies were subsequently restreaked on R5 plates with lincomycin (200 μ/mL) and without thiostrepton and incubated at 39° C.

Because the autonomous plasmid cannot efficiently replicate at the elevated temperature, this temperature shift selects for clones that harbor a chromosomally integrated copy of the plasmid. Homologous recombination between one (or both) of the two plasmid borne actinorhodin gene fragments flanking ermE with its presumed identical counterpart in the host chromosome leads to integration in the actinorhodin gene cluster. The twelve resulting colonies were restreaked approximately every three days for a period of three weeks at the elevated temperature. Two clones were obtained that failed to exhibit the characteristic blue phenotype, indicative of a lack of actinorhodin production, and were sensitive to thiostrepton at 30° C. These colonies were pink, due to the synthesis of undecylprodigiosin, another antibiotic known to be produced by *S. lividans*. This phenotype is consistent with a deletion of the actinorhodin gene cluster due to two recombination events between the homologous actinorhodin gene fragments. Only one of these two clones sporulated well, however, and after verification, this clone was identified as strain K27-39.

To demonstrate that candidate clone obtained indeed carried a deletion (rather than, e.g., a point mutation) PCR analysis was performed. PCR using primers 1 and 2 (Table 1, supra) leads to the synthesis of a 700 bp ermE gene fragment. PCR using primers 3 and 4 (Table 1, supra) generates a 900 bp fragment that extends from the 3' region of the actinorhodin ketosynthase/acyltransferase gene (actI-ORF1; see Fernandez-Moreno et al., supra) to the 5' region of the actinorhodin chain length factor gene (actI-ORF2; see Fernandez-Moreno et al., supra). This analysis indicated that the correct construct was obtained.

Production of 6-dEB in K27-39 transformants comprising a recombinant erythromycin PKS gene is approximately equal to that observed in CH999, K-4-114, and K4-155 cells comprising the same recombinant gene, demonstrating that K27-39 cells are suitable for the recombinant production of commercially important polyketides.

EXAMPLE 5

Increasing Polyketide Production with the ptpA Gene

A. Cloning of ptpA Gene

Genomic DNA from *Streptomyces coelicolor* CH1 and from *Streptomyces lividans* TK24 was used as template for amplifying by PCR and cloning the ptpA gene. The primers used for the PCR were primer PTPA5'NDEI, which has a sequence defined by SEQ ID NO. 5: 5'-GGGCATATGACCTACCGCGTCTGTTTCG (shown with the NdeI restriction enzyme recognition site underlined and the ATG start codon of the ptpA open reading frame in bold), and primer PTPA3'XBAI, which has a sequence defined by SEQ ID NO. 6: 5'-GGGTCTAGATCATGCCGCCCGTCCTTCCAC (shown with the XbaI restriction enzyme recognition site underlined and the TCA stop codon of ptpA in bold, although the non-coding strand is depicted). The coding strand of the open reading frame of the ptpA gene is depicted from start to stop in SEQ ID NO. 7: ATGACCTAC-CGCGTCTGTTTCGTGTGCACGGGCAA-CATCTGCCGCTCCCC GATGGCCGAGGCCGTCTTC-CGCGCGCGCGTGGAAGACGCCGGGCTCGGC CACCTCGTCGAGGCAGACAGCGCCGG-TACCGGCGGCTGGCACGAGGGA GAGGGCGCA-GACCCGCGCACCGAGGCCGTGCTGGCG-GACCACGGTTACG GCCTCGATCACGCGGCCCGGCAGTTC-CAGCAGTCCTGGTTCTCCCGCCTC GACCTG-GTCGTCGCCCTCGACGCCGGTCATCT-GAGGGCCCTGCGGCGCCT CGCCCCCACGGAGCGGGACGCGGCCAAG-GTGCGTCTGCTGCGGTCGTAC GACCCCGCG-GTCGGGGCGGCGACCTGGACGTCCCG-GACCCGTACTACG GGGGCCGGGACGGCTTCGAGGAATGCCT-TGAGATGGTGGAGGCGGCGAG CACCGGACT-GCTCGCCGCGGTACGCGAGCAAGTG-GAAGGACGGGCGGC ATGA Pfu polymerase was used to catalyze the PCR; thus, the fragments generated had blunt ends. A single band (from each reaction) was generated and cloned into the EcoRV restriction enzyme recognition site of plasmid pZero2.1, which is commercially available from Invitrogen, 1600 Faraday Avenue, Carlsbad, Calif. 92008. The bands, each of ~510 bp in size, were cloned into pZero2.1. The resulting plasmids were designated pKOS027-21 (TK24 fragment) and pKOS027-22 (CH1 fragment). Both inserts were subsequently sequenced and found to be identical to each other and to the published sequence by Li and Strohl, supra (accession #: U37580). Plasmids pKOS027-21 and pKOS027-22 harbor the cloned ptpA PCR fragment in the same orientation: in both cases the NdeI site of the PCR fragment is next to the NotI site of the pZero2.1 vector, and the XbaI site of the PCR fragment is next to the PstI site of the pZero2.1 vector. This orientation is required to cut out the ~520 bp NdeI—EcoRI fragment desired for purposes of constructing the expression vector. Hence, pKOS027–21 and pKOS027-22 are identical.

Both fragments were transferred into an expression vector derived from pSET152 (available from the U.S. Dept. of Agriculture, Agricultural Research Service Midwest Area, National Center for Agricultural Utilization Research, 1815 N. University St., Peoria, Ill. 61604, under the accession No. NRRL B-14792). This vector integrates into the host chromosome; transcription of the cloned gene is under the control of the actI promoter. The resulting expression constructs were designated pKOS027-26 (CH1 gene) and pKOS027–28 (TK24 gene). These two plasmids are presumed to be identical.

Plasmid pKOS027-26 contains the following 4 DNA fragments: (i) the large EcoRI-XbaI restriction fragment of vector pSET152 (see also Bierman et al., 1992, *Gene* 116:43–49; both enzymes cut once in the polylinker region); (ii) an ~30 bp XbaI-HindIII fragment from the polylinker region of the commercially available plasmid pLitmus28 (New England Biolabs, Inc., 32 Tozer Road, Beverly, Mass. 01915-5599); an ~3 kb HindIII-NdeI restriction fragment from plasmid pRM5 (McDaniel et al., 1993, *Science* 262:1546–1550; and U.S. Pat. No. 5,672,491, both of which are incorporated herein by reference), which contains the transcriptional terminator fd, the actII-ORF4 activator gene, the actinorhodin ketoreductase gene, and the actI promoter region; and an ~520 bp NdeI—EcoRI restriction fragment containing the CH1-derived ptpA gene from plasmid pKOS027-22. Plasmid pKOS027-28 contains the same 4 DNA fragments, except the latter fragment is derived from plasmid pKOS027-21.

Streptomyces strain CH999 was transformed with both plasmids and transformants selected by resistance to apramycin. The resulting apramycin resistant strains were transformed with several DEBS expression constructs by additional selection for thiostrepton resistance. Production levels were analyzed from cultures grown on plates and from liquid cultures.

B. Increased Polyketide Production from ptpA Coexpression and Diketide Feeding

Plasmid pJRJ2 is described in U.S. patent application Ser. No. 896,323, filed Jul. 17, 1997, incorporated herein by reference. This plasmid encodes an active site mutated module 1 ketosynthase domain of eryAI (DEBS 1 gene) and so is unable to synthesize 6-dEB using the normal starting materials. However, when Streptomyces CH999 host cells containing plasmid pJRJ2 are provided with activated diketide precursors, the corresponding 6-dEB or 13-substituted 6-dEB compounds are produced.

The procedure for feeding diketides follows.

I. Inoculum Development

1. Add 2.5 mL of complete R5 medium to a sterile glass culture tube containing 2 glass beads.
2. Add either thiostrepton only to 50 µg/ml (pJRJ2) or both apramycin to 60 µg/ml and thiostrepton to 50 µg/ml (pJRJ2 +pKOS027-26) to the respective culture tube for the strain being cultivated.
3. Inoculate the tube using an inoculation loop containing approximately 5 $mm^2$ of culture from an agar plate.
4. Incubate the tube at 30° C. and 250 RPM for 48 hours.
5. Check the progress of growth daily and shake down the ring of mycelia that forms on the side of the tube.

II. Transfer to Production Medium

1. Prepare SO1 medium. SO1 medium contains: 51.5 g sucrose; 0.25 g $K_2SO_4$; 0.1 g casamino Acids; 5.0 g yeast extract; 5.73 g TES buffer; 0.96 g propionic acid; 2 mL trace elements; and distilled water to 1 L; after autoclaving, the following components are added: 10 mL $KH_2PO_4$ (0.5%); 8 mL $CaCl_2$ (2.5 M); 7.5 mL L-proline (20%); 7 mL NaOH (1 N).
2. Add 2.5 mL of SO1 medium to sterile tubes containing 2 glass beads.
3. Add either thiostrepton only to 50 µg/ml (pJRJ2) or both apramycin to 60 µg/ml and thiostrepton to 50 µg/ml (pJRJ2 +pKOS027-26) to the SO1 medium.
4. Inoculate the tubes containing SO1 with 50 µL of inoculum.
5. Incubate the tube at 30° C. and 250 RPM for 5 days. Check on the progress of growth daily and shake down the ring of mycelia that forms on the side of the tube.

III. Diketide Feeding

1. For each 2.5 mL of SO1 medium add: 150 µL of propyl-diketide solution [4.67 mg/mL in 10% DMSO] 25 µL of 4-pentynoic acid [2.5 mg/mL in MQ water]
2. Solutions of 4-pentynoic acid must be stored at $\leq -20°$ C. and prepared every 2 weeks.
3. After feeding diketide, incubate the cultures at 30° C. and 250 RPM for 5 days.

IV. Product Recovery and Assay

Sample preparation with extraction for 2.5 mL cultures:

1. After 5 days, put 500 µL of culture into a clear eppendorf tube.
2. Add 500 µL of ethyl acetate (EtOAc) and vortex at maximum speed for 5–10 seconds.
3. Centrifuge the tube at 13×1000 RPM for 3 minutes. Transfer the solvent to a glass culture tube (12×75 mm).
4. Repeat steps 2 and 3 two more times.
5. Evaporate to dryness using a speed vacuum concentrator at 35° C. for 20–30 minutes.
6. Resuspend in 200 µL of acetonitrile and transfer the sample to a plastic autosampler vial (12×32 mm).
7. Label the sample accordingly. Note the run-time, conditions, and injection volume on the in-process form.
8. Run LC/MS by injecting 20 µL of each sample.

Thus, in one experiment CH999 host cells containing ptpA and pJRJ2 (designated CHptp, below) were compared in polyketide product levels to CH999 host cells containing only pJRJ2 after diketide feeding and fermentation. The results are summarized in Table 3 below.

TABLE 3

Polyketide Production

| Strain | ELSD Peak Area | μg in Peak | Titer mg/L | Average |
|---|---|---|---|---|
| CHptp-3 | 1133 | 13.92 | 278.43 | 224 |
|  | 433 | 5.48 | 109.52 |  |
|  | 1151 | 14.14 | 282.77 |  |
| CHptp-8 | 656 | 8.17 | 163.33 | 163 |
|  | 700 | 8.70 | 173.95 |  |
|  | 608 | 7.59 | 151.75 |  |
| CHptp-9 | 1103 | 13.56 | 271.19 | 172 |
|  | 610 | 7.61 | 152.23 |  |
|  | 360 | 4.60 | 91.90 |  |
| CH999-7 | 270 | 3.51 | 70.19 | 72 |
|  | 382 | 4.86 | 97.21 |  |
|  | 180 | 2.42 | 48.47 |  |
| CH999-4 | 904 | 11.16 | 223.17 | 129 |
|  | 349 | 4.46 | 89.25 |  |
|  | 290 | 3.75 | 75.01 |  |

Thus, the overall average (ptpA—186, without ptpA—101) shows an almost two-fold increase in the amount of erythronolide product produced under the conditions of this test.

C. Increased Polyketide Production from ptpA Coexpression in Recombinant Host Cells While the increased yield of polyketides produced with ptpA expression and diketide feeding is an important embodiment of the present invention, the methods of the present invention are equally applicable to increasing the yield of a naturally occurring polyketide or to polyketides produced in recombinant host cells. The following test results illustrate the invention as applied to recombinant polyketide production.

CH999 cells transformed with recombinant vector pKOS011-13, which produces a 3-keto analog of 6-dEB, and either with or without a recombinant ptpA gene were grown on plates, and the amount of polyketide produced was measured. The control CH999 cells produced 0.4 mg/mL, while cells containing either pKOS027-26 (two clones, both producing 1.9 mg/L) or pKOS027-28 (two clones, one producing 2.4 mg/L and the other 2.2 mg/L) produced about 5-fold more polyketide than the control cells.

In another test, the recombinant polyketide synthase was encoded on plasmid pKOS011-64, which makes 10,11-anhydro 6-dEB, and an ~3-fold increase (as measured by chromatographic peak area: area of 94 for control and area of 285 for cells with pKOS011-64 and pKOS027-26) was observed. In another test, with the same cells and vectors, an almost 100-fold increase was observed (control cells: area of 16; cells with pKOS011-64 and pKOS027-26: area of >1573-out of range).

These tests show that ptpA co-expression increases production levels of recombinant polyketides, such as 6-dEB-related compounds.

Other tests demonstrated that the increased production levels could be achieved with a recombinant vector that encoded a naturally occurring PKS gene sequence. In one test, CH999 cells harboring plasmid pKAO127'Kan' produced 15 mg/L of 6-dEB, while CH999 cells harboring plasmids pKAO127'Kan' and pKOS027-28 produced 84 mg/L 6-dEB, an ~5-6 fold increase.

These tests show that ptpA co-expression increases production levels of polyketides produced by recombinant host cells, regardless of whether the polyketide synthase codes for a naturally occurring polyketide or a novel polyketide produced through genetic engineering techniques.

The invention having now been described by way of written description and examples, those of skill in the art will recognize that the invention can be practiced in a variety of embodiments and that the foregoing description and examples are for purposes of illustration and not limitation of the following claims.

What is claimed is:

1. A *Streptomyces lividans* host cell that can be transformed with methylated DNA and that does not produce actinorhodin and that further lacks the ability to recombine plasmid DNA with other plasmid DNA.

2. The *Streptomyces lividans* host cell of claim 1 that further comprises a recombinant phosphotyrosine protein phosphatase, ptpA, gene.

3. A *Streptomyces lividans* host cell that can be transformed with methylated DNA and that does not produce actinorhodin and that further comprises a recombinant ptpA gene.

4. The *Streptomyces lividans* host cell of claim 3 that is K4-114 which has been transformed with a recombinant ptpA gene.

5. A method for the production of a polyketide in a *Streptomyces coelicolor* or *Streptomyces lividans* host cell, which host cell contains recombinant modular polyketide synthase genes, said method comprising the steps of:
   (a) transforming said host cell with a recombinant vector that comprises a ptpA gene capable of expression in said host cell; and
   (b) culturing said host cell, transformed in step (a), under conditions such that said ptpA gene is expressed and said polyketide is produced;
wherein said polyketide is produced by a recombinant modular polyketide synthase encoded by said recombinant modular polyketide synthase genes.

6. The method of claim 5, wherein said host cell is the *Streptomyces coelicolor* strain CH999.

7. The method of claim 5, wherein said host cell is the *Streptomyces lividans* strain K4-114.

8. A method for the production of a polyketide in a *Streptomyces coelicolor* or *Streptomyces lividans* host cell, which host cell contains recombinant 6-deoxyerythronolide B synthase genes, said method comprising the steps of:
   (a) transforming said host cell with a recombinant vector that comprises a phosphotyrosine protein phosphatase, ptpA, gene capable of expression in said host cell; and
   (b) culturing said host cell transformed in step (a) under conditions such that said ptpA gene is expressed and said polyketide is produced;
wherein said polyketide is selected from the group consisting of:
   (i) 6-deoxyerythronolide B,
   (ii) 3,6-dideoxy-3-oxo-6-deoxyerythronolide B, and
   (iii) 10,11-anhydro,6-deoxyerythronolide B.

9. The method of claim 8, wherein said polyketide is 6-deoxyerythronolide B.

10. The method of claim 8, wherein said polyketide is 3,6-dideoxy-3-oxo-6-deoxyerythronolide B.

11. The method of claim 8, wherein said polyketide is 10,11-anhydro,6-deoxyerythronolide B.

12. The method of claim 5, wherein said host cell is a *Streptomyces lividans* host cell that can be transformed with methylated DNA and that does not produce actinorhodin and that further lacks the ability to recombine plasmid DNA with other plasmid DNA.

13. The method of claim 12, wherein said recombinant modular polyketide synthase genes are encoded on a plasmid in said host cell.

* * * * *